United States Patent
Tillander

(10) Patent No.: US 6,676,104 B2
(45) Date of Patent: Jan. 13, 2004

(54) DEVICE FOR CONTROLLING THE FLOW OF LIQUID USING A TUBE

(75) Inventor: Hans Tillander, Humlegårdsgatan (SE)

(73) Assignee: Premetec AB, Vastra Frolunda (SE)

( * ) Notice: Subject to any disclaimer, the term of this patent is extended or adjusted under 35 U.S.C. 154(b) by 0 days.

(21) Appl. No.: 10/299,275

(22) Filed: Nov. 19, 2002

(65) Prior Publication Data

US 2003/0116730 A1 Jun. 26, 2003

Related U.S. Application Data

(63) Continuation of application No. PCT/SE01/01138, filed on May 21, 2001.

(30) Foreign Application Priority Data

May 19, 2000 (SE) ................................................ 0001852

(51) Int. Cl.$^7$ ................................................ F16K 7/02
(52) U.S. Cl. ................................................ 251/4; 251/7
(58) Field of Search ....................................... 251/4–10

(56) References Cited

U.S. PATENT DOCUMENTS

| 3,773,034 A | * | 11/1973 | Burns et al. ............. 604/95.01 |
| 4,478,434 A | * | 10/1984 | Little .......................... 285/15 |
| 4,671,320 A | | 6/1987 | Grifols Lucas |
| 5,913,861 A | * | 6/1999 | Trotta ...................... 604/96.01 |

FOREIGN PATENT DOCUMENTS

EP 0 045 668 6/1981

* cited by examiner

*Primary Examiner*—Paul J. Hirsch
(74) *Attorney, Agent, or Firm*—Samuels, Gauthier & Stevens, LLP

(57) ABSTRACT

The present invention relates to a device containing a tube for a varied flow, comprising a tube being fixed in both its ends, whereby the tube is arranged to be stretched or shortened by longing or shortening of the distance between said attachment points.

6 Claims, 1 Drawing Sheet

DEVICE FOR CONTROLLING THE FLOW OF LIQUID USING A TUBE

This is a continuation of PCT/SE01/01138, filed May 21, 2001.

DESCRIPTION

1. Technical Field

The present invention relates to a device with an elastic tube for a varied flow through said tube, whereby the device comprises a tube being fixed at its two ends.

The object of the present invention is to obtain a device with an elastic tube by means of which device a predetermined, varied and controllable flow through the tube, can be obtained.

2. Background of the Invention

It is previously known different peristaltic pumps, in particular for pumping small volumes, which pumps comprise a tube arranged on the inside of a circular house against which tube a number of rolls are arranged to act rotatably and by means of their rotation press a liquid through the tube. The flow volume through the tube is dependent on the rotational speed of the rolls against the tube.

It is further known valve devices at infusion tubes for regulating the flow through the tube. It has, however, turned out that these valves do not provide a constant flow and do not provide reproducible flows.

DESCRIPTION OF THE PRESENT INVENTION

It has now surprisingly turned out possible to be able to obtain a reproducible, varied and controllable flow by means of the present invention which is characterized in that the tube is arranged to be stretched by means of a longing of the distance between its points of attachment.

Further characteristics are evident from the accompanying claims.

By means of the present invention it is obtained that the flow can be varied in a very efficient and accurate way which is particularly essential at infusions where great demands for a constant flow is due, in order not to e.g., overdosing at a drug infusion.

Figure 1:
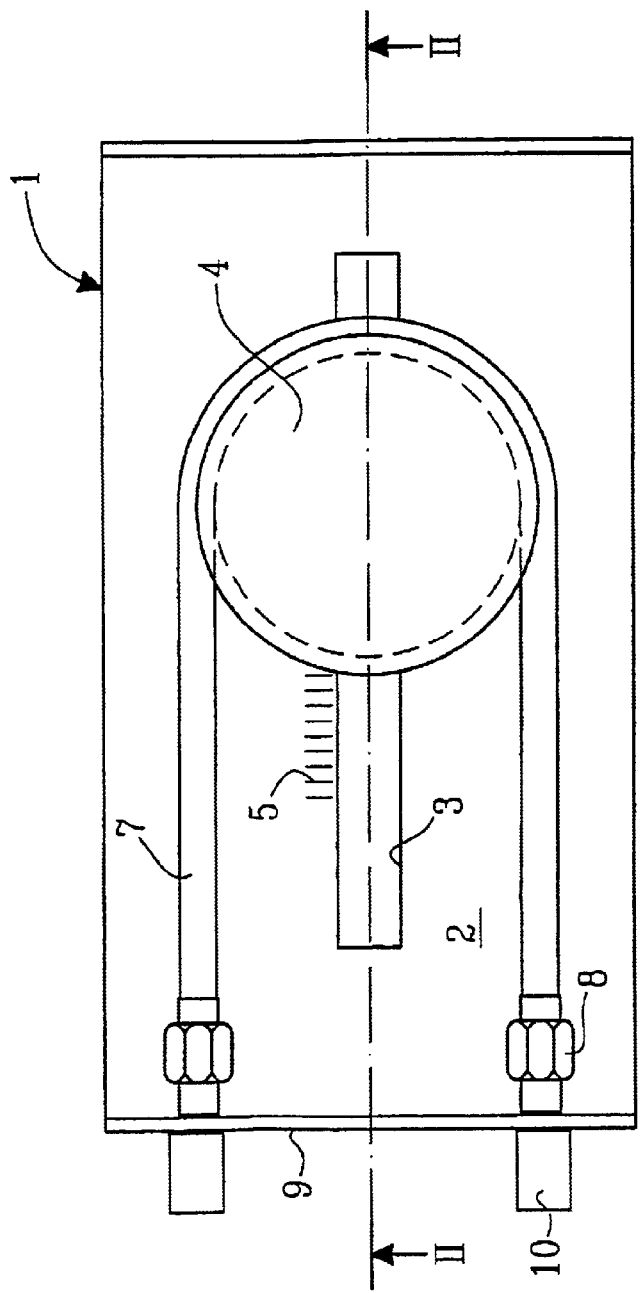
Figure 2:
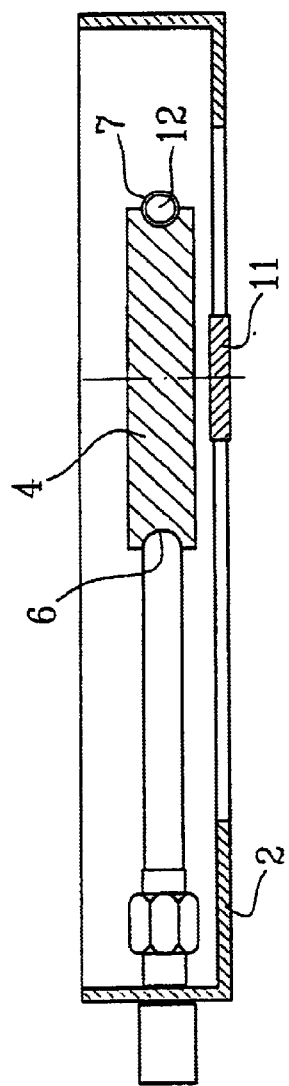

The present invention will now be described more in detail with reference to the attached drawing, which shows a preferred embodiment, however, without being restricted hereto. In the drawing FIG. 1 shows a device according to the invention seen from above; and FIG. 2 the device of FIG. 1 seen in a cross-sectional view along the line II—II.

1 denotes in general a house which in its bottom part 2 is provided with a track 3. In the track 3 there is a wheel 4 movably arranged. Position markings 5 are further arranged along the track 3. The wheel 4 is suitably provided with an arcuate recess 6 in which a tube 7 is arranged to be introduced. The tube 7 which is suitably a silicone polymer tube, is at its two ends releasably attached to two nipples 8 arranged in the short end side 9 of the house 1. The nipples 8 are provided with through-going holes (not shown) for communicating with nipples 10 arranged on the outside of the house 1, which nipples are arranged to be connected to a liquid container and e.g., a patient, respectively, via a tube (not shown). Underneath the wheel 4 in the track 3 there is a screw 11 arranged for the fixation of the wheel 4 in a desired position.

When the wheel 4 is moved along the track 3 the tube 7 is strained and is stretched due to its elastic properties. Simultaneous with the stretching, the lumen 12 of the tube 7 will be reduced as well, which conclusively means that the flow will become down-regulated from a first less stretched condition to a second more stretched condition.

The volume flow at laminar flow is $$\frac{V}{t} = k \frac{\Delta p \cdot D^4}{l}$$

V=volume t=time $\Delta p$=pressure fall between the ends of the tube $D^4$=forth potence of the diameter of the lumen of the tube l=the length of the tube $k=\pi/128\eta$, wherein $\eta$ is the dynamic viscosity of the liquid The formula means that the flow is reciprocally proportional to the length of the tube but proportional to the fourth power of the diameter of the tube. The diameter of the tube thus plays a dominating role and at small liquid flows and, particularly at liquids comprising particles, such as blood, which is commonly present in medical situations, it is thus difficult to control the flow only by means of changing the diameter of the tube. The change becomes exponential and extremely small changes of the diameter of the tube provides great changes of the liquid flow which is evident from the attached graph. The changed of the length of the tube provides a more even change of the flow but is hard to carry out from a practical point of view. A simultaneous change of the length of the tube and diameter will thus become more optimal.

By successively straining an elastic tube, one will simultaneously obtain, together with a longing of the tube, a narrowing of the lumen which provides an optimal and almost linear control of the liquid flow.

In the trial given below an elastic tube being 180 mm long and having a lumen of 0.5 mm. The pressure fall was 0.1 mbar. Each step in the following flow table means a longing of 8 mm.

TABLE

| Change of length from 180 mm | Flow ml/hr |
|---|---|
| 0 | 420 |
| 2 | 390 |
| 4 | 360 |
| 6 | 330 |
| 8 | 300 |
| 10 | 270 |
| 12 | 240 |
| 14 | 210 |
| 16 | 180 |
| 18 | 150 |
| 20 | 120 |
| 22 | 90 |
| 24 | 60 |

As evident from the results provided an almost linear change of the flow amount is obtained which means an assumption for an exact dosage of the flow at small flow amounts without using a compulsory pump function with the drawbacks this leads to.

By adopting the length of the tube, the wall thickness of the tube, the lumen diameter, and the elastic construction to get a widespread utilization.

What is claimed is:

1. A device containing a tube for a varied flow, comprising a tube being fixed at its both ends, wherein the tube is arranged to be stretched or shortened by lengthening or shortening of the length of the tube between said fixed points, whereby the device comprises at least one arc shaped surface arranged to receive said tube, that the arc shaped surface is arranged to be adjustably moved in a longitudinal direction for longing or shortening said tube, and whereby the arc shaped surface is at least one wheel provided with a radially inwardly directed recess for receiving said tube.

2. A device according to claim 1, wherein the tube is an infusion tube.

3. A device according to claim 1, wherein the tube is of an elastic material.

4. A device according to claim 3, wherein the tube is a silicone material tube.

5. A device according to claim 1, wherein the tube is arranged in a system to control the flow through the same.

6. A process for controlling a flow through a tube, wherein one stretches or relaxes an elastic tube between two attachment points via at least one arc shaped surface arranged to receive said tube, the arc shaped surface being arranged to be adjustably moved in a longitudinal direction for lengthening or shortening said tube, and whereby the arc shaped surface is at least one wheel provided with a radially inwardly directed recess for receiving said tube, for on one hand lengthening or shortening said tube, on the other hand narrowing or widening its lumen.

* * * * *